United States Patent
Malin et al.

[11] Patent Number: 5,377,002
[45] Date of Patent: Dec. 27, 1994

[54] APPARATUS FOR SURFACE INSPECTIONS

[75] Inventors: Comas Malin, Mauren, Liechtenstein; Edgar F. Steigmeier, Hedingen, Switzerland; Thomas Nesensohn, Batschuns, Austria; Harry L. Sawatzki, Schaan, Liechtenstein; Heinrich Auderset, Aeugst; Gert Schmid, Thüringen, both of Switzerland

[73] Assignee: Tet Techno Trust Investment Settlement, Liechtenstein

[21] Appl. No.: 913,592

[22] Filed: Jul. 14, 1992

[30] Foreign Application Priority Data

Jul. 20, 1991 [CH] Switzerland .................. 02154/91-7
Feb. 26, 1992 [EP] European Pat. Off. ........ 92103251.2

[51] Int. Cl.⁵ .......................................... G01N 21/00
[52] U.S. Cl. .................................. 356/237; 356/371; 356/426; 250/572
[58] Field of Search .................. 356/237, 371, 426; 250/572, 235, 236

[56] References Cited

U.S. PATENT DOCUMENTS

| | | | |
|---|---|---|---|
| 3,229,564 | 1/1966 | Meltzer | 356/448 |
| 3,565,568 | 2/1971 | Hock | 356/369 |
| 4,197,011 | 4/1980 | Hudson | 356/237 |
| 4,391,524 | 7/1983 | Steigmeier et al. | 356/237 |
| 4,526,468 | 7/1985 | Steigmeier et al. | 356/237 |
| 4,598,997 | 7/1986 | Steigmeier et al. | 356/237 |
| 4,659,220 | 4/1987 | Bronte et al. | 356/237 |
| 5,048,967 | 9/1991 | Suzuki et al. | 356/237 |
| 5,108,176 | 4/1992 | Malin et al. | 356/243 |
| 5,127,726 | 7/1992 | Moran | 356/237 |
| 5,135,303 | 8/1992 | Uto et al. | 356/237 |

*Primary Examiner*—Robert J. Warden
*Assistant Examiner*—Hien Tran

[57] ABSTRACT

This apparatus permits the non-destructive examination of entire surfaces for defects and contamination, and can detect microscopically small dot-shaped and linear defects and extremely fine macroscopic non-homogeneous areas. For this purpose, an adjustable lens system (5) is placed in the optical path between light source (2) and objective (9) which produces various intermediate images (31). A first cigar-shaped intermediate image is used for the first scan of the whole of the surface at a relatively large feed offset, and a second dot-shaped intermediate image is used for a second scan of partial areas of the surface at a small feed offset.

A dark-field stop assembly (18) with an adjustable dark-field deflection system (8) is placed in the optical path between the lens system (5) and the objective (9), which projects the light beam (1) after deflection exactly centered at right angles through the objective (9) upon the surface of the object (10). The light reflected by the surface (10) and collected by the objective (9) is projected to a photo detector. An electronic analysis system (21) breaks down the amplified output signals from the photo detector (19) into measured values due to dot-shaped, linear, and planiform defects. The electronic analysis system (21) is connected via a computer unit (22) to peripheral equipment (23, 24, 25) which permits the representation of all the measured values obtained in a measuring cycle.

28 Claims, 13 Drawing Sheets

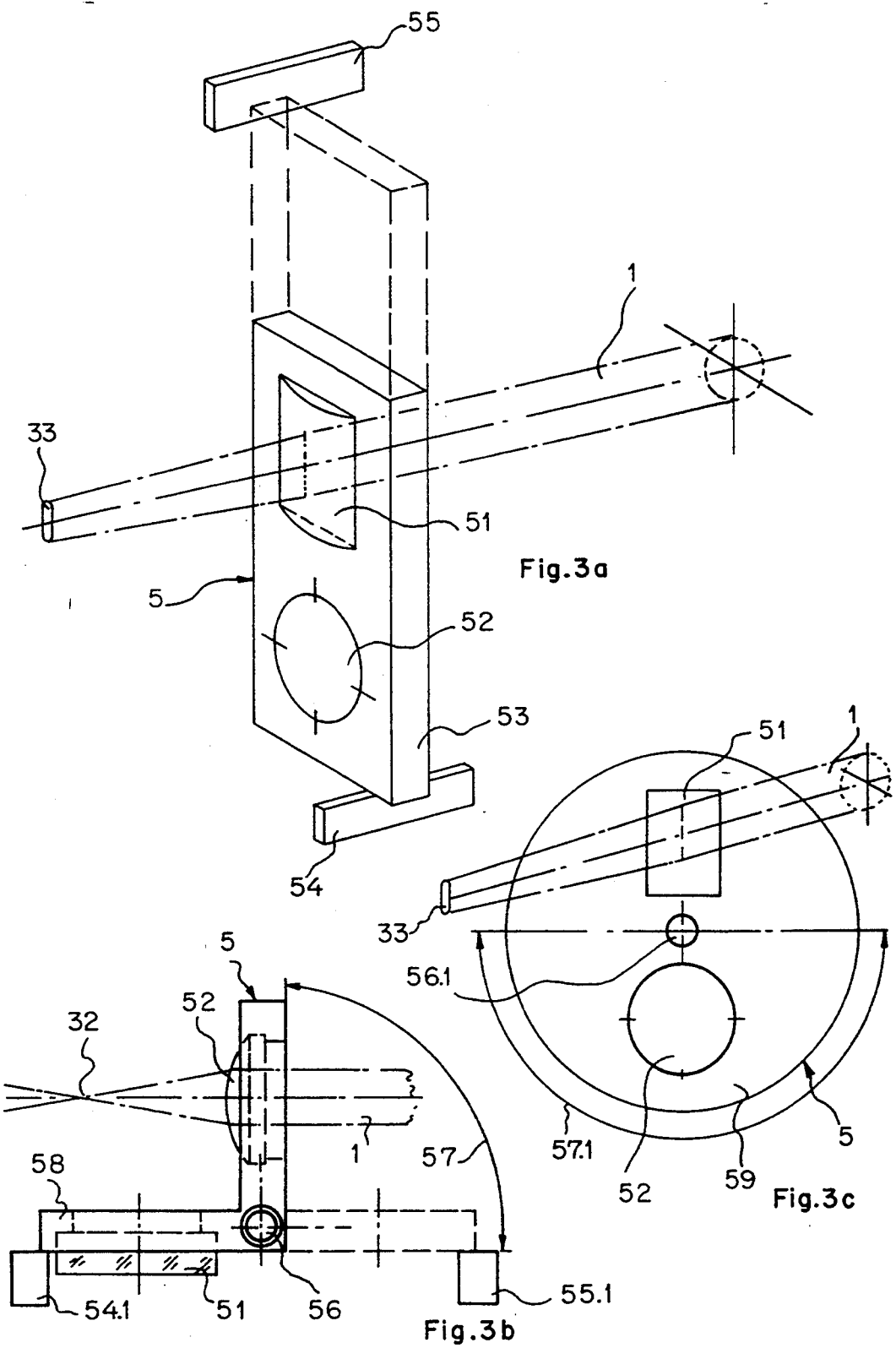

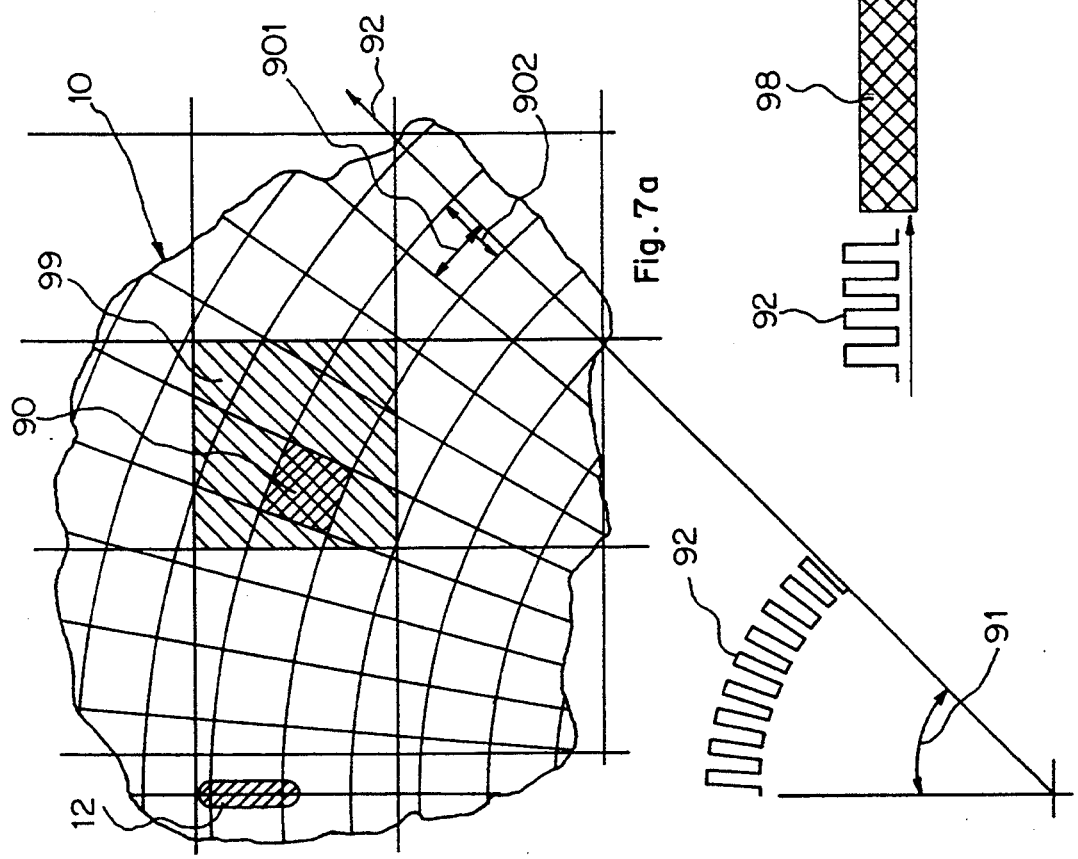

APPARATUS FOR SURFACE INSPECTIONS

BACKGROUND OF THE INVENTION

The present invention relates to an apparatus for the examination and inspection of surfaces by means of a light source that generates a light beam, which has an objective and a supporting disk on which the object for inspection can be placed, wherein the light beam through the objective is perpendicular to the surface of the object and the supporting disk is secured to a drive that can make a composite rotational and translational movement so as to permit the light beam to scan the surface of the object along a spiral path, with provision for a photo detector to which the light reflected by the surface of the object and collected in the objective is directed and whose output is connected to an amplifier.

Such apparatuses can be used, for example, in microelectronics for the non-destructive examination and inspection of the surface of wafers, magnetic storage media, and substrates for optical applications, in order to determine the presence of defects.

PRIOR ART

U.S. Pat. No. 4,314,763 relates to an apparatus with the above attributes, in which a beam of light from a light source in the form of a laser is projected via two prisms and an objective perpendicularly upon the surface of an object for examination and/or inspection. The object is secured to a support connected to the shaft of a spur-gear drive. The spur-gear drive is fitted to a plate which can be moved in a straight line by a motor. For the inspection of an object's surface, the rotational movement of the support and the translational movement of the plate are superimposed upon each other so that the light beam through the fixed optical system scans the surface of the object under inspection along a spiral path. The beams diffused and diffracted by the surface are directed via the objective to a photo detector which sends an electrical signal to an amplifier when the beam illuminates a defect. The amplifier is connected to a counter and a cathode-ray screen. The counter counts the number of amplified electrical signals, corresponding to the number of defects detected, and the cathode-ray screen shows their spatial distribution.

Because such apparatuses are highly sensitive, due in part to the fact that the static optical system must form an image in the photo detector of diffused light in only a small illuminated area, they can determine and recognize not only spherical particles, but also linear and planiform defects of an order of magnitude down to about 1 μm. Because of the good imaging properties that a corrected objective of high optical quality can achieve and due to the circumstance that the diffused light from the illuminated area is collected within an angle of 360° and imaged in the photo detector, such apparatuses achieve high efficiency in the detection of diffused light.

Such apparatuses as described above must at the same time be extremely sensitive and provide a high measuring speed. Limiting factors are the finite mechanical scanning speed, on the one hand, and the greater bandwidth necessary in the measuring system as the speed increases. The finiteness of the scanning speed is given by the holding device used for the substrate, the bearings and drive for the substrate support, and the material of the substrate itself. The need for greater bandwidth as the measuring speed increases is given by the fact that the signal from a defect becomes shorter as the speed increases, at which it moves in relation to the illuminated area. As the bandwidth increases, the amplifier and photon noise also increases. In practice, photon noise mitigates against greater bandwidth.

As measuring speed increases, it is essential to ensure that there is no reduction of the high local resolution necessary for the analysis of defects. High local resolution permits an accurate reproduction of the track of a defect and measurement of its exact position on the surface. A precise knowledge of the location of the area for inspection and its accurate dimensions are extremely useful, especially for the analysis of defects, for example by means of an electron microscope, after the inspection itself.

BRIEF SUMMARY OF THE DISCLOSURE

The object of the present invention is an apparatus that permits higher local resolution at the same time as greater measuring sensitivity and speed than the prior art referred to above.

The present invention meets these requirements in having a lens system placed in the optical path between light source and objective. This lens system is adjustable in various positions, and depending on its position, it produces different intermediate images. For the first scan of an object, a first intermediate image is used, and for the second scan, a second intermediate image. The feed offset for scanning is adjusted in accordance with the intermediate image used. A dark-field stop assembly placed in the optical path between the lens system and the objective, and having an adjustable dark-field deflection system, projects the light beam after deflection exactly centred through the objective and perpendicularly upon the object to be inspected.

To process the measured data, an electronic analysis system is provided whose input side is connected to the photo detector's downstream amplifier. These analyzer electronics break down the output signal generated by the amplifier into measured values that originate in the dot-shaped, linear, and planiform defects on the surface of the object under examination or inspection.

A system that can determine the light beam's effective scanning position on the surface of the object at any moment is connected to peripheral equipment that can represent in their entirety and in their respective scanning positions all the measurements obtained in a given test.

The present invention thus achieves the following advantages:
Switching of the lens system permits the inspection of either the whole of the surface or parts thereof, as required.
In scanning, the astigmatic light beam produced by the switchable lens system covers a larger area and thus permits a larger feed offset from one revolution to the next. On the other hand, the dot-shaped light beam is used with a small feed offset and makes possible high local resolution.
The apparatus can be used to inspect and represent any partial area of the surface.
It permits a free choice of the size of the partial area inspected.
Measurement of a partial area of the surface is accompanied by an increase in measuring sensitivity by comparison with the measurement of the whole of the surface.

The apparatus can quickly and by non-destructive means recognize, locate, and quantify all the usual defects on surfaces and in regions near the surface, such as dot-shaped defects (LPDs=light-point defects), linear (line) defects, and planiform defects (haze).

The measured results can be represented in any required orientation, for example relative to the flat on the wafer.

The results of the measurements of a partial area of the surface are represented as an upright image.

Typical embodiments of the invention proposed by the present disclosure are described in conjunction with the drawings, as follows:

BRIEF DESCRIPTION OF DRAWINGS

The file in this patent contains at least one drawing executed in color. Copies of this patent with color drawings will be provided by the Patent and Trademark Office upon request and payment of the necessary fee.

FIG. 3a, 3b, 3c are three typical embodiments of switchable lens systems of the apparatus in accordance with the first embodiment as shown in FIG. 1;

FIG. 5b is a detailed representation of a part of the analyzer electronics shown in FIG. 5a;

FIG. 7a is a diagrammatic representation of part of the surface of an object and its subdivision into imaginary areas for measurement;

FIG. 7b is a diagrammatic representation of a table for the addresses assigned to the imaginary areas for measurement shown in FIG. 7a;

FIG. 7c shows part of the pixel area required to represent the measurements obtained from the areas shown in FIG. 7a;

FIG. 8b is a typical measured image of a partial area of the surface of FIG. 8a;

DETAILED DESCRIPTION OF THE INVENTION

Figure 1:
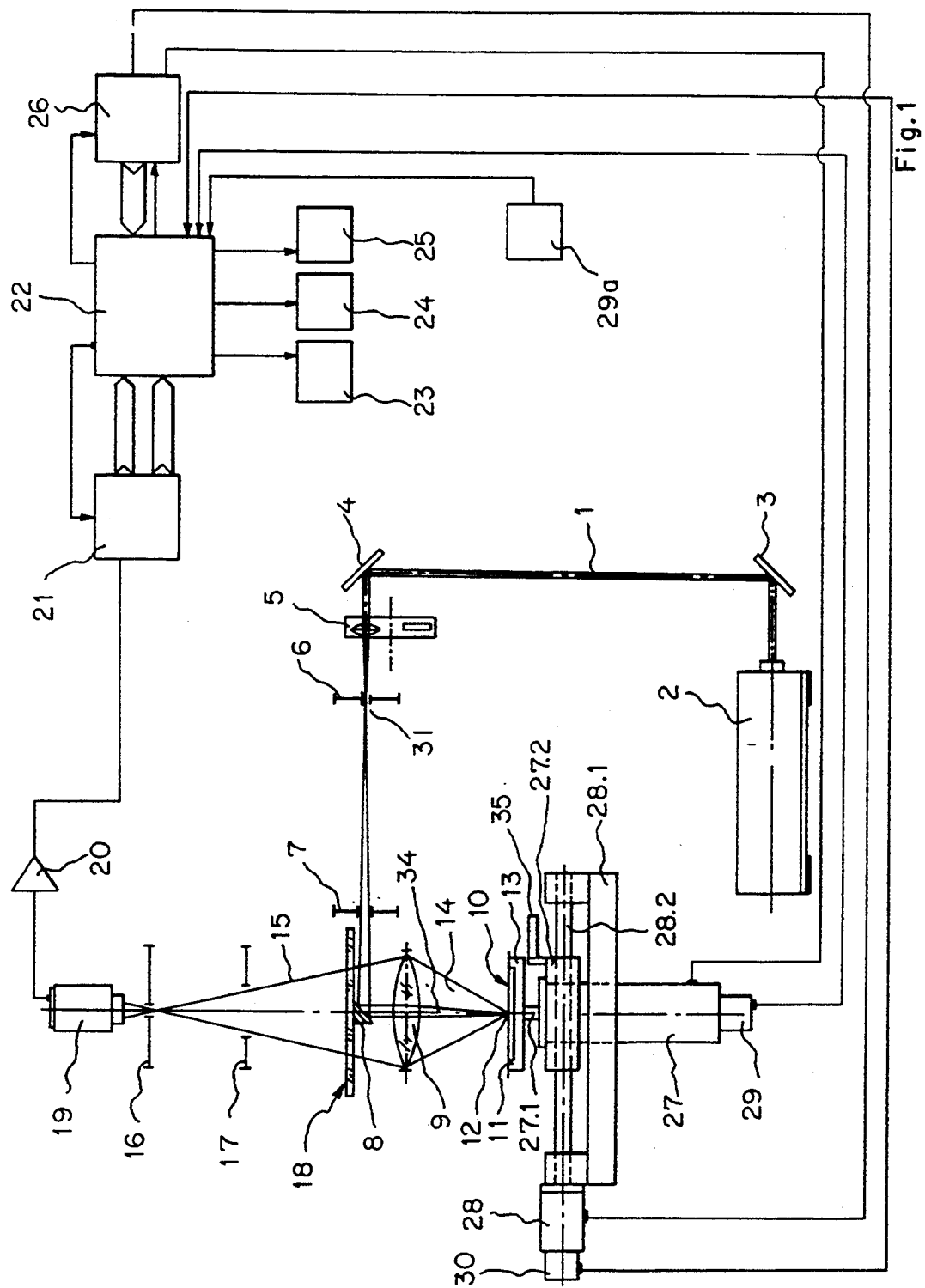
FIG. 1 is a diagrammatic representation of a first typical embodiment of the apparatus covered by the present disclosure.

In FIG. 1, a first embodiment of the apparatus covered by the present disclosure, 1 indicates a light beam from a light source 2, where light source 2 is a laser that emits light of very short wavelength, for example 488 nm or 325 nm.

A light beam 1 is projected via deflecting mirrors or prisms 3, 4; an adjustable lens system 5 in accordance with FIGS. 3a, 3b, 3c, and hereinafter described in further detail; diaphragms 6, 7; a dark-field deflection system 8; and an objective 9. It strikes the surface 10 of an object, in the form of a substrate 11, on which it forms a spot of light 12. The substrate 11 is placed on a supporting disk 13 that lies on a plane perpendicular to the light beam 1. 14 indicates a cone of diffused light (FIG. 2a, 2b, 2c) reflected by the surface 10, and 15 a light cone collected by the objective 9. The front diaphragm 17 and a confocal diaphragm 16 project the light cone 15 upon a photo detector 19 which is connected via an amplifier 20 to the analyzer electronics 21, as described in greater detail by FIGS. 5a and 5b. The analyzer electronics 21 are connected to a computer unit 22, which in turn is connected to peripheral equipment, such as a mass-storage system 23, monitor 24, and printer 25. 18 indicates a dark-field stop assembly, as described in greater detail by FIGS. 4a, 4b, and 4c, which has a dark-field deflector 8. The supporting disk 13 is connected to the shaft 27.1 of a rotary motor 27 which is fixed to a linear stage 27.2. The linear stage 27.2 sits on a spindle 28.2 borne by a bearer 28.1; a translation motor 28 drives the spindle 28.2. The rotary motor 27 and the translation motor 28 are connected by an interface 26 to the computer unit 22. A rotation-pulse emitter 29 coupled to the shaft of the rotary motor 27, an encoder used as a translation-pulse emitter 30 and coupled to the shaft of the translation motor 28, and a pulse generator 29a in the form of an electronic rectangular-pulse generator are connected to the computer unit 22. Components 27, 27.1, 27.2, 28, 28.1, and 28.2 form a drive which produces a combined rotation and translation movement. 31 indicates an intermediate image generated by the adjustable lens system 5, and 34 is the optical axis of the objective 9. The linear stage has a photosensitive device 35 below the supporting disk 13.

Figure 2A:
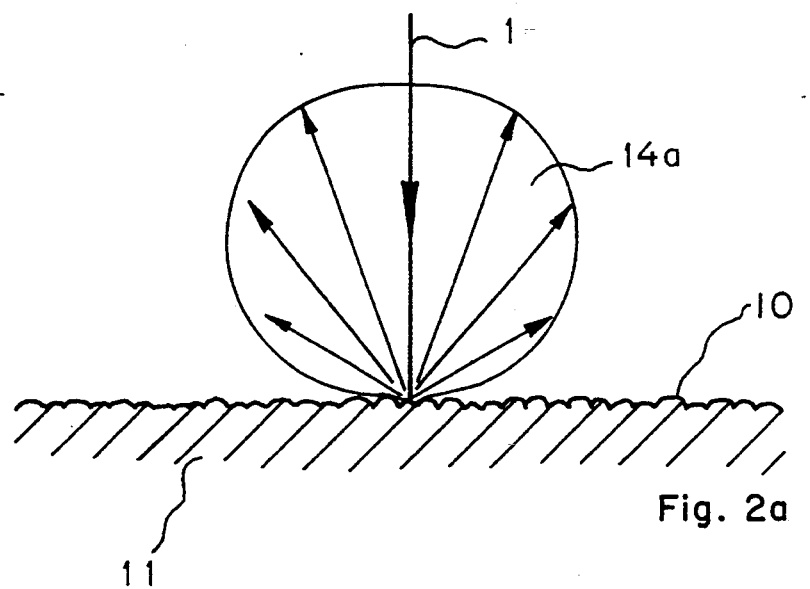
FIG. 2a, 2b, 2c are simplified representations of the brightness distribution of diffused light typical of a surface with a high haze level (2a), a low haze level (2b), and a hypothetical surface without defects and perfect reflection (2c)
Figure 2B:
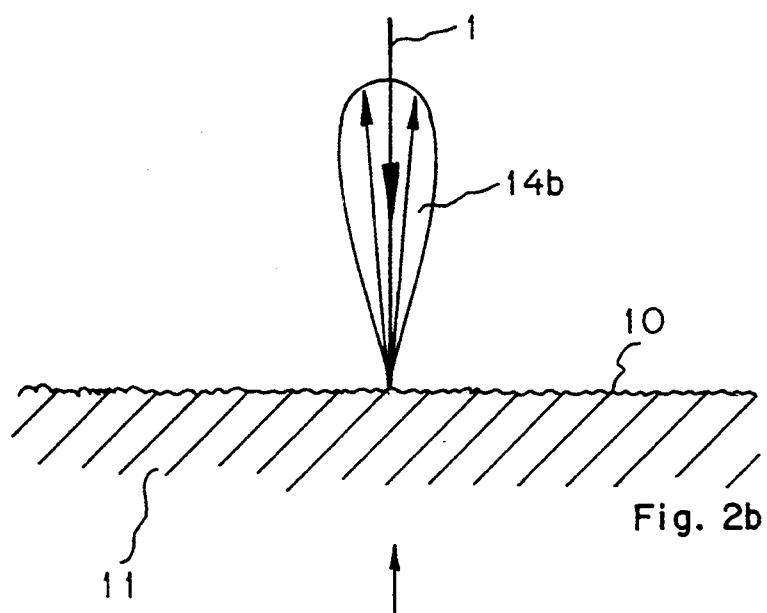
Figure 2C:
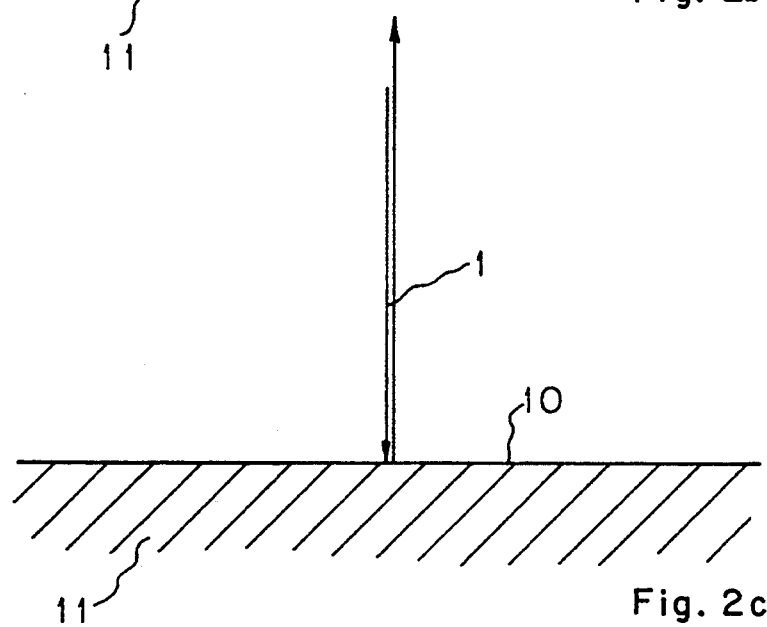

FIG. 2a shows that the brightness distribution of light diffused by surfaces with physically large defects is flatter and more parallel to the surface 10 and thus the cone 14a of diffused light is broader; FIG. 2b shows that surfaces with physically small, dense diffusing centres have a narrower diffused-light cone which lies closer to the axis 14b. In FIGS. 2a and 2b, the cones of diffused light 14a, 14b consist of the light from the beam 1 which the surface 10 diffuses, diffracts, and reflects. The change from broad diffused-light cones 14a to narrower diffused-light cones closer to the axis 4b is due to the fact that increasingly perfect surfaces whose diffusing centres are ever smaller manifest an increasing characteristic of forward diffusion, so that, in extreme cases (FIG. 2c), only reflection of the light beam 1 is obtainable.

FIGS. 3a, 3b, and 3c show the lens system 5 consisting of at least two lenses 51, 52 which can be moved interchangeably in the light beam 1. One of these lenses forms an astigmatic intermediate image 33. The first of these lenses should preferably be a cylindrical lens 51 and the second a spherical lens 52. The two lenses have the same focal length, thus when they are moved into the light beam 1, the first intermediate image of either lens is in the same plane. When the cylindrical lens 51 is moved into the beam, it forms a cigar-shaped first intermediate image 33; when the spherical lens is placed in the beam, it forms a dot-shaped second intermediate image 32.

Figure 7D:
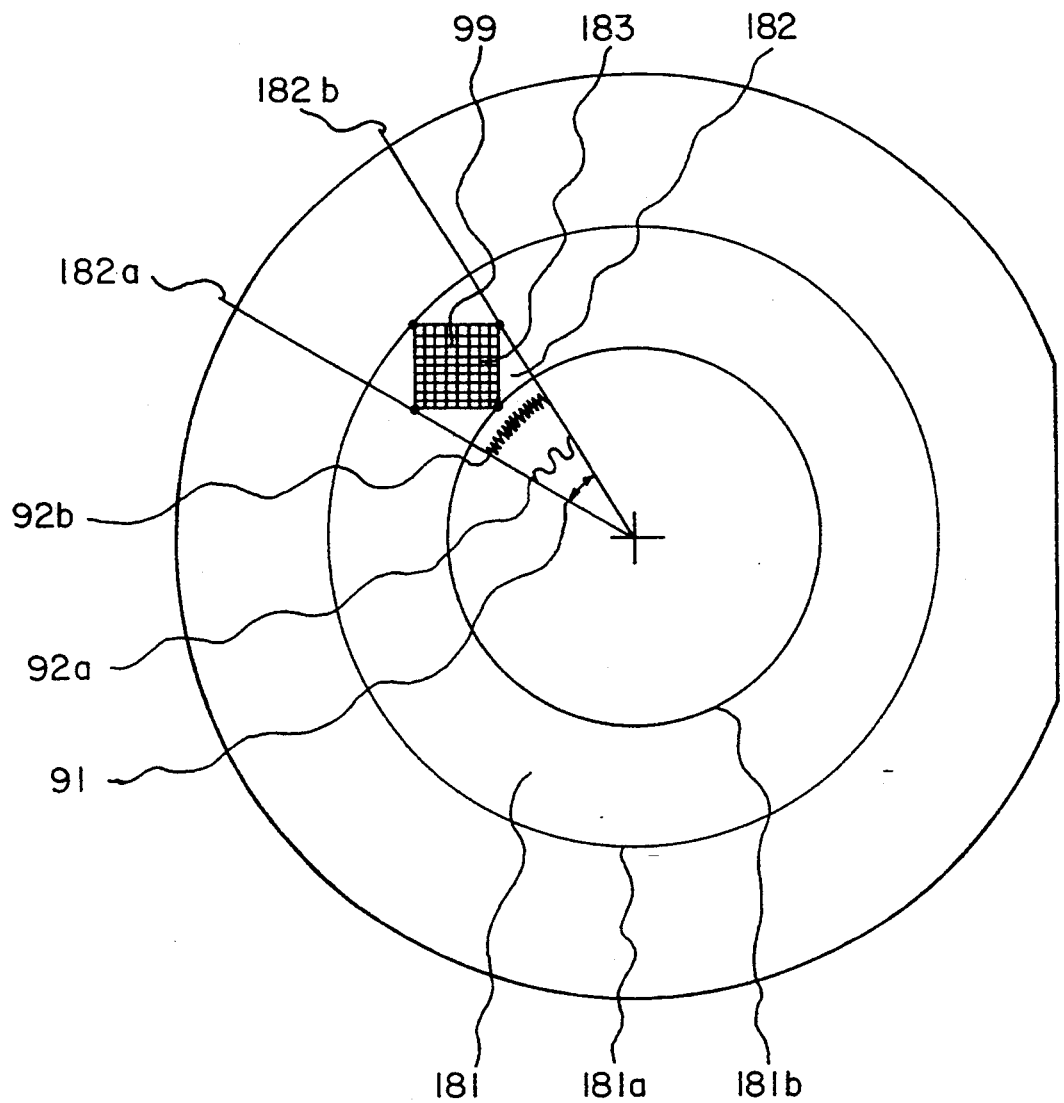
FIG. 7d is a diagrammatic representation of a measuring cycle for the measurement of a partial area of the surface.

The light spot 12 generated by the cigar-shaped astigmatic light beam 1 covers a larger area of the rotatably driven object when the major axis of the cigar shape is aligned in the radial direction as shown in FIG. 7a and therefore permits a larger feed offset from each revolution to the next. A dot-shaped light beam is smaller and its luminous density is greater. It is therefore used with a smaller feed offset for the examination of the surface with high local resolution, similar to a scanning laser-beam microscope. The dot-shaped light beam 1 should preferably be used only for the inspection of selected portions of the surface.

FIG. 3a shows the two lenses 51, 52 fitted to a slide 53 so that they can be moved alternatively by a linear movement into the light beam 1. The lenses 51, 52 are adjustable relative to each other in a manner not shown. Adjustable stops define the position of the lenses 54, 55 after the linear movement.

FIG. 3b shows the lenses 51, 52 on a pivot 56 placed perpendicular to the light beam 1 so that they are pivotable by a given pivot angle 57. In this case the lenses 51, 52 are fitted into an L-shaped carrier plate 58. The angle of the L-shaped carrier plate is equal to the pivot angle 57. Stops 54.1, 55.1 again define the end positions.

FIG. 3c shows the lenses 51, 52 fitted to a disk 59 that can be rotated on its axis 56.1 which is parallel to the light beam 1. In this case the lenses can be moved by rotation about an angle 57.1 into the light beam 1.

Electric motors, electric rotary or lifting magnets, or compressed-air drives such as linear or rotary cylinders may be used to drive the lens systems. For unambiguous identification of the correct positioning of the lens after it is moved into position, the stops may be equipped with end switches or inductive approximation switches which permit position monitoring by the electronic control system.

Figure 4A:
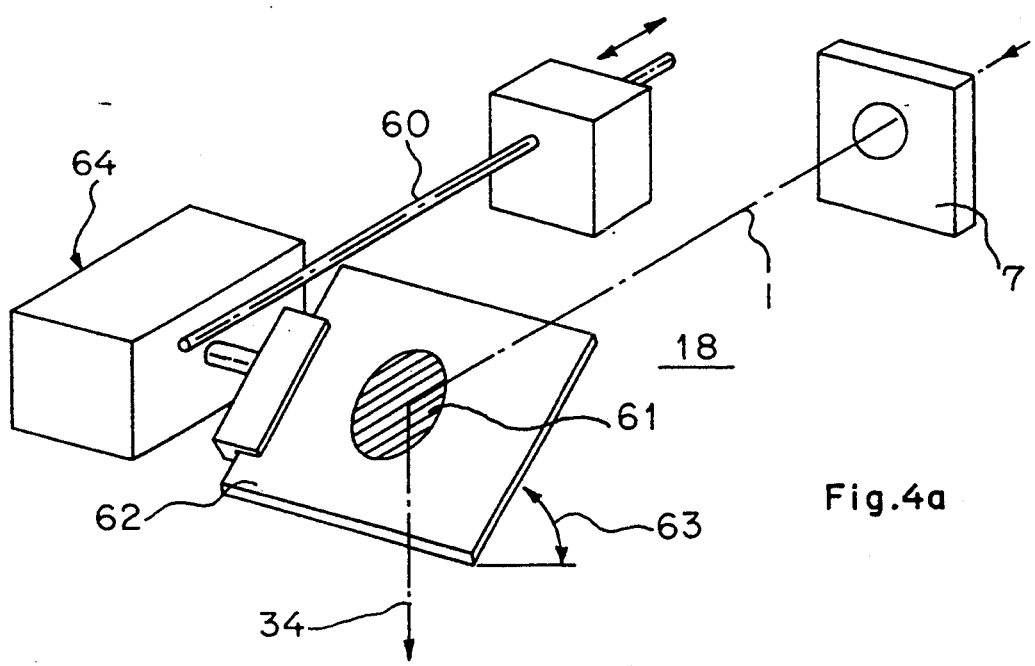
FIG. 4a, 4b, 4c are three embodiments of a dark-field stop assembly for an apparatus made in accordance with the first embodiment as shown in FIG. 1.

FIG. 4a shows the dark-field stop assembly 18 with a dark-field stop 61 directly integrated in the dark-field stop's carrier plate 62 and corresponding to the dark-field deflection system 8 (FIG. 1). The centre of the dark-field stop's carrier plate is coated with a material that reflects the light of beam 1. The shape of the dark-field stop's reflecting surface 61 must be such as to produce a circularly symmetrical projection of the dark-field stop assembly 18 along the optical axis 34. At an angle of inclination 63 greater than 0°, the shape of the reflecting surface is that of an elliptical disk. The dark-field stop's carrier plate 62 itself is made of material such as glass or quartz glass that transmits the light beam's wavelengths. The surfaces of the dark-field stop and the dark-field stop's carrier plate may be optically coated to optimize transmission.

The dark-field stop's carrier plate 62 is so secured mechanically to a mount 64 as to permit adjustment of the beam by displacement or rotation. This adjustment may be by setscrews (not shown). In this case, clamping screws (not shown) permit final positioning.

Figure 4B:
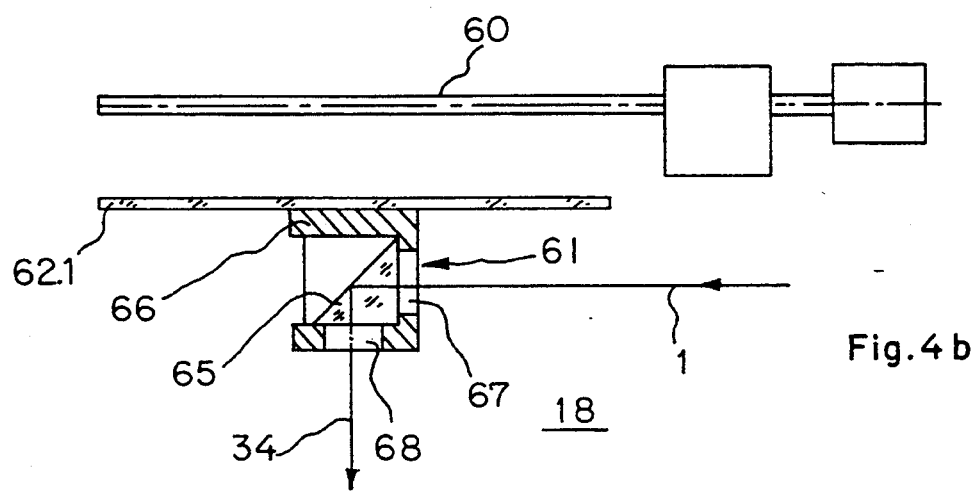

The dark-field stop 61 shown in FIG. 4b is formed by a prism 65. In this case the oblique prism surface provides total reflection to deflect the light beam 1. A prism mount 66 fixed to the dark-field stop's carrier plate 62.1 holds the prism 65. The prism mount 66 is cylindrical to ensure a circularly symmetrical projection along the image-forming system's optical axis 34. The light beam 1 passes through a first opening 67 in the prism mount 66. This first opening 67 and a second opening 68 prevent the passage of unwanted light in the edge zones of the light beam 1.

Figure 4C:
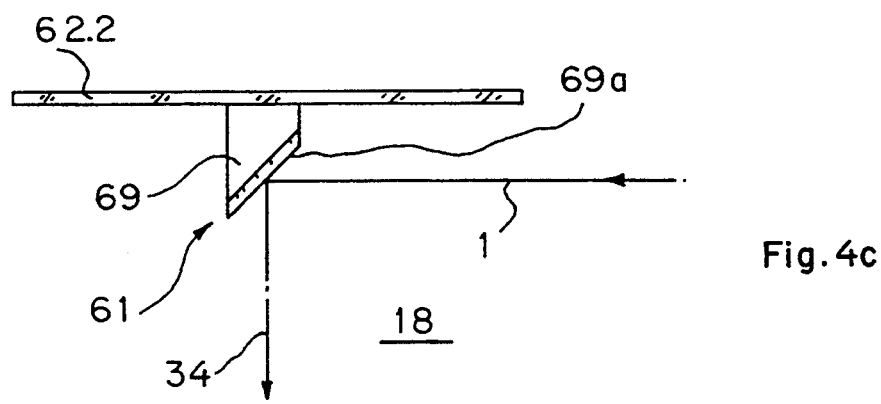

FIG. 4c shows the light beam 1 deflected by the silvered oblique surface of a cylindrical body 69 fixed to a carrier plate 62.2 for the dark-field stop.

The position of the dark-field stop's carrier plates 62.1, 62.2 in FIGS. 4b and 4c is also adjustable. By comparison with the first embodiment, these embodiments have the advantage that the reflecting surface of the dark-field stop 61 can be brought closer to the objective (FIG. 1). The closer the position of the dark-field stop 61 to the objective 9, the smaller is the vignetted area in the diffused-light cone and thus the better is the solution.

In FIGS. 4a and 4b, a vignetting device 60 permits the introduction of asymmetry into the image-forming optics, if required. Dual measurement, for example, with and without this vignetting device 60, makes it possible to distinguish between oriented and random haze structures. For the identification of one-dimensional defect structures such as polishing defects, this vignetting device 60 is rod-shaped. For the selective suppression or recognition of other structures, other forms of vignetting device 60 can be used.

The optical part of the apparatus described above functions as follows:

The light beam 1 is deflected by prisms 3, 4 and passes the astigmatic lens system 5 and diaphragms 6, 7 to the dark-field deflection system 8, which in turn deflects it. The dark-field deflection system 8 and the dark-field stop 61 are so adjusted as to ensure that after deflection the deflected light beam 1 passes exactly centred and at a right angle through the objective 9 so that its path after deflection is exactly along the optical axis 34 of the objective and thus of the entire image-forming optical system. The objective 9 focuses the light beam 1 on the substrate's surface 10 so as to project upon the surface 10 of the substrate the intermediate image 31 produced by the lens system 5. Because the light beam 1 strikes the substrate perpendicularly to its surface 10, the surface 10 reflects the light exactly along the incident light beam 1 so that it again passes through the objective back to the dark-field stop 61, which in turn deflects it back to the light source 2. The diffused and deflected part of the light 14 are collected under the angle of the numerical aperture of the objective 9 and imaged in the confocal diaphragm 16. The distance between the surface 10 and the aperture of the confocal diaphragm 16 is equal to the adjustable distance between the intermediate image 31 and the surface 10.

Very dense and very fine defect textures of surface defects known as haze produce a certain amount of diffracted light in addition to diffused light. This light should be understood as diffraction by a grid or grating formed by a texture, due to defects such as polishing defects. The light cone of the light thus produced has no locally homogeneous brightness distribution. At the site of the dark-field stop assembly 18 the brightness distribution of the light is thus rotationally symmetrical in relation to the optical axis 34 and may therefore, for example, form propeller- or star-shaped patterns. The orientation of this brightness distribution is strictly related to the orientation of the surface texture 10, i.e. if the substrate is rotated, the brightness pattern rotates synchronously with it.

For the measurement of surface textures due to defects, regardless of orientation, the dark-field stop assembly 18 is rotationally completely symmetrical in construction in relation to the optical axis 34. Further, to allow the passage of diffused light close to the optical axis, that proportion of the diffused-light cone 14 effectively blocked by the dark-field stop 61 must be as small as possible. The apparatus described makes it possible to obtain the most favourable ratio of collected to vignetted diffused light. The light in the image retains its full rotational symmetry.

The objective 9 focuses the diffused light 14 on the confocal diaphragm 16. The shape of the aperture of this confocal diaphragm 16 is approximately the same as that of the light beam focused on the surface of the substrate as light spot 12. When the cylindrical lens 51 is in position, the shape of the light spot 12 is oblong, with its major axis 202 radial and its minor axis 204 tangential. To produce an oblong shape of light spot, the aperture of the confocal diaphragm 16 is a slit whose dimensions are about the same as the size of the light spot multiplied by the magnification factor of the image-forming optics. The advantage of this is that only the diffused light from the site illuminated by the light beam 1 can reach the photo detector 19 through the diaphragm's aperture. In practice this manifests itself by the fact that the apparatus is insensitive to ambient light and has a good signal-to-noise ratio. To produce a circular shape of light spot, the aperture of the confocal diaphragm 16 is a circle whose diameter is about the same as the diameter of the light spot multiplied by the magnification factor of the image-forming optics. Switching between different confocal diaphragms can be performed in a manner similar to that used for switching between lenses in the adjustable lens system 5.

One or more front diaphragms 17 in the image-forming section prevent unwanted stray light reaching the photo detector 19, for example due to reflection from components. The front diaphragms also improve the signal-to-noise ratio and, as in the case of the special-shape confocal diaphragm 16, enhance the measuring sensitivity of the apparatus.

A photo detector 19 converts the optical signals into electronic signals. A broad-band amplifier 20 then amplifies them for further processing. The signal at the amplifier output is the sum of the signals produced by haze, light-point defects, and line defects. Further processing has to separate this combined signal into its components. First of all, the analyzer electronics 21 process the electronic signal by breaking down the input signal into haze and LPD signals.

Figure 5A:
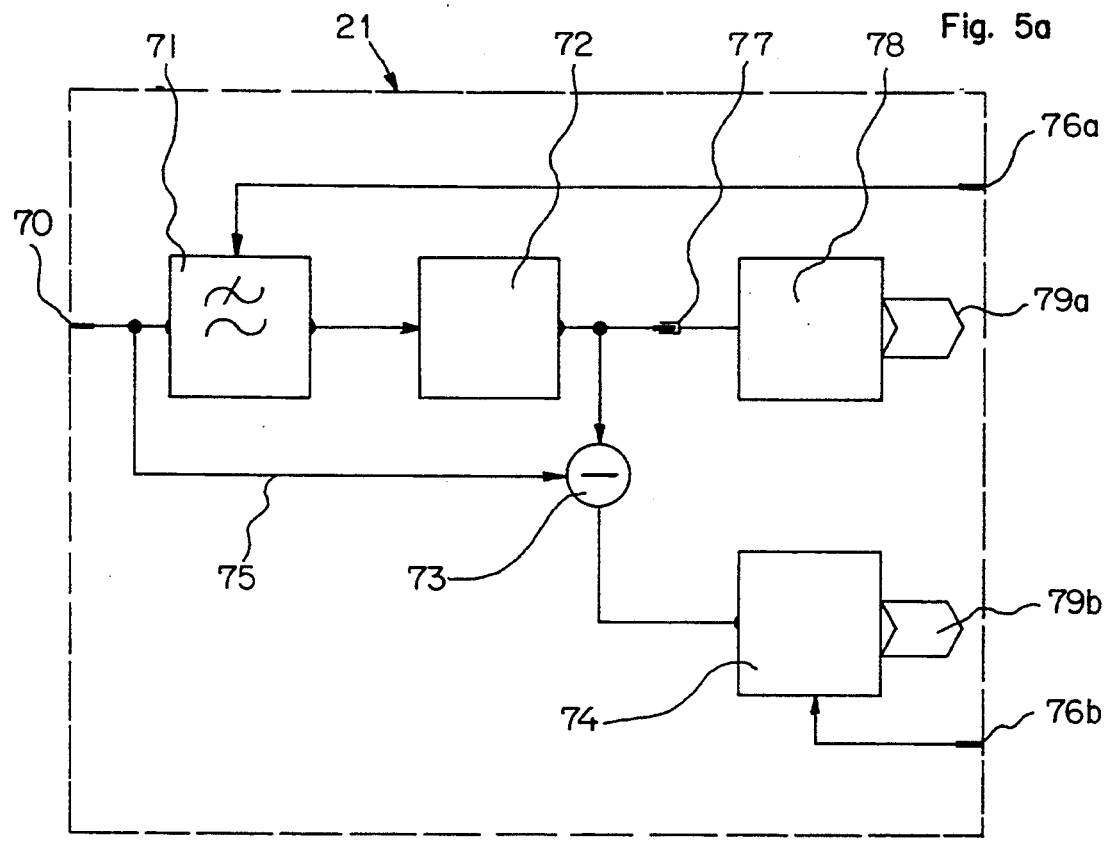
FIG. 5a is a block diagram of the analyzer electronics for an apparatus made in accordance with the first embodiment as shown in FIG. 1.

FIG. 5a shows the analyzer electronics 21 with a signal input 70 connected to the output from the amplifier 20 (FIG. 1) and to a haze channel which consists of a haze filter 71 and a peak suppressor 72. The signal input 70 is also connected to a particle channel which consists of a subtraction circuit 73 and a peak detector 74. A nominal-bandwidth input 76a is connected to the haze filter 71, and a further input 76b is connected to the peak detector 74. A haze-filter output 77 is connected to an analog-digital converter 78, whose output is indicated as 79a. The peak detector 74 has a digital output 79b.

Figure 5B:
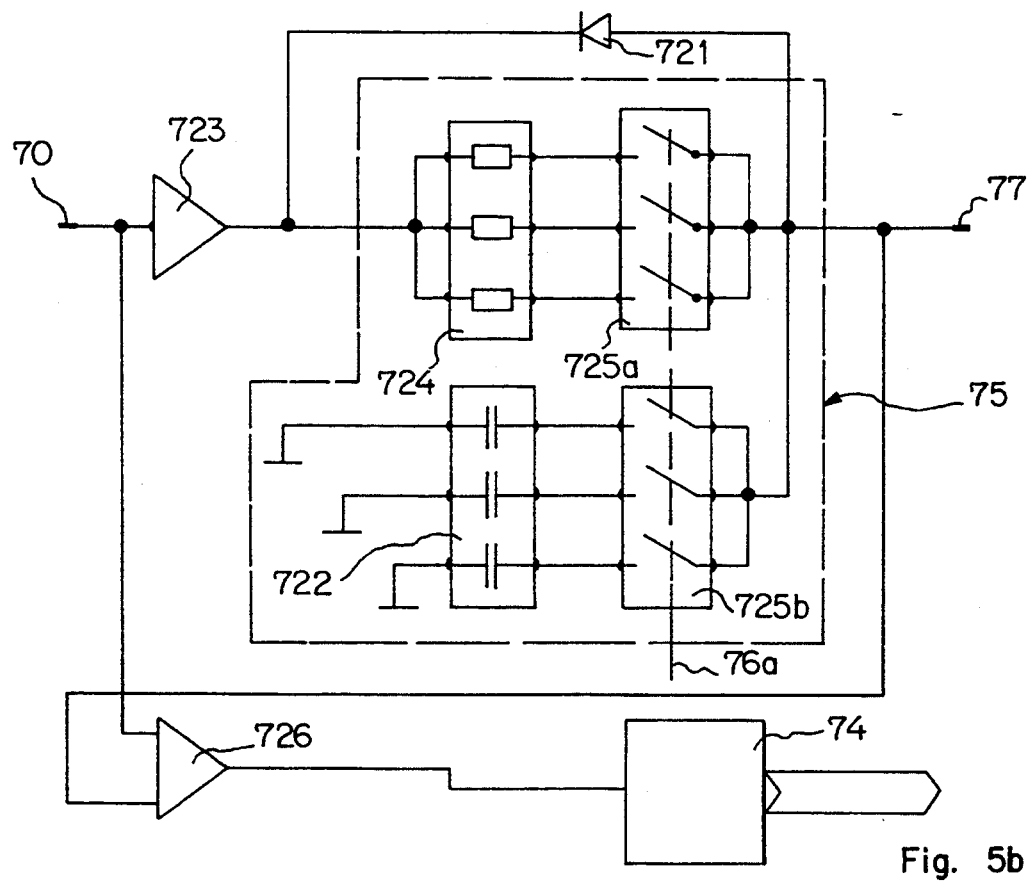

In FIG. 5b, the main element of the haze channel 71, 72 (FIG. 5a) is a low-pass filter 75 which consists of filter condensers 722, resistors 724, a first switch system 725a, and a second switch Aystem 725b. One end of the resistors 724 is connected via the first and second switch systems 725a and 725b to the filter condensers 722 and the haze-filter output 77 (FIG. 5a). Via a diode 721 which acts as a peak suppressor 72, the haze-filter output 77 is connected to the other ends of the resistors 724 and the output of a second amplifier 723. The input of the second amplifier 723 is connected to the signal input 70 (FIG. 5a) and the non-inverting input of a third amplifier 726 which acts as subtractor 73 (FIG. 5a). The inverting input of the third amplifier 726 is connected to the haze-filter output 77, and its output is connected to the input of the peak detector 74. The nominal-bandwidth input 76a controls the operation of the switch systems 725a, 725b.

Figure 6A:
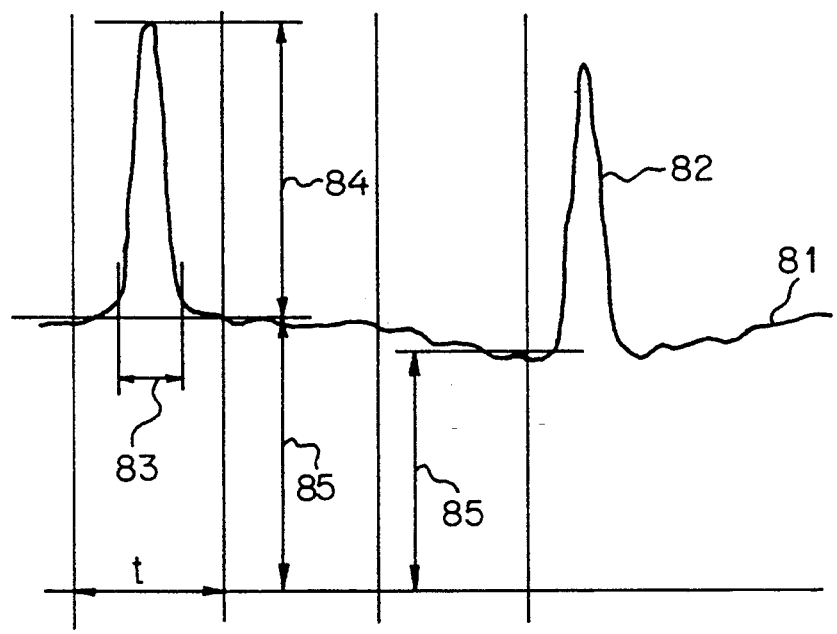
FIG. 6a, 6b show typical graphs of the signals at the photo detector, obtainable with an apparatus made in accordance with the first embodiment shown in FIG. 1, on the edge of an object under inspection (6a) and in the centre of the object (6b)
Figure 6B:
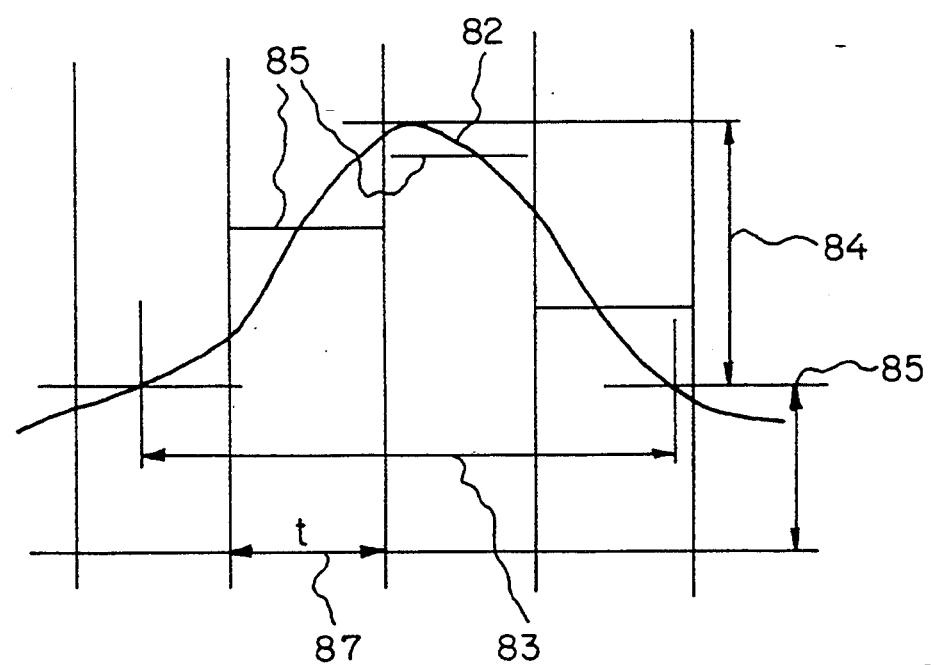

The analyzer electronics described above function as follows:

The analyzer electronics 21 distinguish between haze and LPDs by timing the signals (FIG. 6a, 6b). Haze signals 81 change relatively slowly, but LPDs have clearly marked short pulses 82. The low-pass filter 75 allows the low-frequency signals of various forms of haze to pass but suppresses the LPD pulses. The amplitude of the pulses 82 is proportional to the size of the LPD. Because LPDs are relatively small in relation to the light spot, the width 83 of such pulses depends on the spot width and the speed at which the LPDs move relative to the light spot 12. If the rotational movement of the substrate whose surface is under examination is constant, the speed of the surface relative to the light spot 12 varies according to the radius; the substrate's outer edge 11 moves fastest and its centre does not move at all. Toward the substrate's centre, the pulses of LPDs become wider (FIG. 6b), hence, without special provisions, LPDs identified as such by their signal pattern at the edge of the substrate might be classified as forms of haze near the centre and, conversely, forms of haze correctly recognized as such on the inside of the substrate surface might be measured as LPDs near the substrate's edge. This could lead to unacceptable measuring errors. An adjustable low-pass filter 75 eliminates these errors. This filter permits the adjustment of the filter constant in accordance with the radial position and the speed of rotation. At the edge of the substrate, the low-pass filter 75 has a small time constant; at the substrate's centre, the time constant is much greater. For fast rotation, its time constant is small, for slow rotation it is large. The filter constant is adjusted once when the rotation speed is specified, then during measurement by switching or by continual adjustment of the filter constant. The object of this is to achieve a constant relationship between the filter constant and the respective substrate speed. Filter adjustment is effected via the nominal-bandwidth input 76a.

Because the amplitude of LPD signals is several orders of magnitude greater than that of haze signals, a certain amount of inductive interference (=crosstalk) among pulses in the haze channel is unavoidable. This interference can falsify the haze values and, as explained below, also the pulse amplitude as such. Diode 721 acts as peak suppressor and short-circuits the voltage gain due to a pulse after its decay via the filter condenser 722 to the output of the second amplifier 723. This suppresses large voltage differences between the output of the second amplifier 723 and the haze filter's output 77. The analog-digital converter 78 digitizes the haze signal at the haze filter's output 77. In practice, because in haze signals the variations are extremely small and account for less than 1% of the signal amplitude, the analog-digital converter 78 must be capable of high resolution.

LPD and line-defect signals are available at the particle channel's output 79b. The amplitude indicates the size of this type of defect. This amplitude is the pure pulse amplitude 84, i.e. without the haze amplitude 85. Especially in the case of small LPDs, the haze amplitude 85 is often greater than the pulse amplitude 84. It is therefore important to subtract the exact haze value from the input signal before further processing of the LPD's amplitude value. The exact value of the haze amplitude is available at output 77 of the haze filter, as described above. The LPD signal is thus obtained by subtraction of the signal at input 70 from that at output 77 by means of the third amplifier 726 used as a subtraction circuit 73.

The peak detector 74 must meet extremely tough requirements: high linearity, low noise, speed, and extremely short reset times. A digital peak detector meets all these requirements at the same time. This component has an analog input and a digital output 79b at which the digitized maximum signal voltage is immediately available.

The peak amplitude 84 determines whether a measured value refers to haze or to an LPD. For this purpose, the analyzer electronics compare the peak value with a reference value. If the peak value is greater then the reference value, the measured value refers to an LPD and is flagged accordingly.

The measured data available at the outputs of the analyzer electronics 79a, 79b are digitized as haze and LPD data. The computer unit 22 displays and stores these measured data in rapid succession. Two sets of data are thus made available, a set of haze data and another of LPD data.

In addition to the measured data as such, the apparatus also records the positional data for each measured value. From the measured data and the relevant positional data, the diffused-light value can be determined and transmitted for each location on the substrate.

The following describes how positional data are determined, by reference to FIGS. 1, 7a, and 7b:

During measurement the measured values are loaded and digitized at predetermined time intervals. The electronic pulses 92 whose phase is coupled to the rotation of the supporting surface 13 trigger the loading of the measured values. For medium local resolution, the pulses are obtained directly from the rotation-pulse emitter 29. For high local resolution, the pulses from the pulse generator 29a are used. For this, the rotation pulses 92a are generated in a first scan of the whole of the surface at a relatively large feed offset, for which the cigar-shaped first intermediate image 33 is used. In a second detailed scan at a small feed offset, for which the second intermediate image 32 is used, the index pulses 92b are used. The number of index pulses 92b is greater than that of the rotation pulses.

The maximum speed at which data can be recorded determines the maximum frequency of the pulse generator 29a. In practice, the maximum speed is limited by the noise level, which increases with the bandwidth.

The pulses 92a and 92b from the rotation-pulse emitter 29 or from the pulse generator 29a, as the case may be, supply angular information 91 pertinent to a given measurement, and the translation-pulse emitter 30 provides information on the radial position (FIG. 7a, 7b). The translation-pulse emitter 30 may be either a linear incremental encoder or, if a spindle is used as the linear drive, it may be an encoder connected to the shaft of the translation motor 28. The interface 26 regulates the speeds of the rotary motor 27 and the translation motor 28 to ensure that the light spot 12 travels along a regular spiral path on the surface 10.

The rotation-pulse emitter 29 and the translation-pulse emitter 30 thus supply the position for each measured value as polar coordinates. However, the measured results must be represented on a computer monitor 24 or on a computer's printer 25, or stored in a mass-storage medium 23. The measured result consists entirely of a pixel area 93 (FIG. 7c) composed of a number of pixels 99 in one direction 94 (X) and of another number of pixels 99 in the other direction 95 (Y). Each pixel 99 in turn represents a given part of the area 90 of the substrate's surface 10. For this representation and for the software-based processing of the data, the polar coordinates must be converted into cartesian coordinates.

In general measurement, the whole of the surface is scanned along a spiral path, but in detailed measurement at greater local resolution, scanning is limited to a ring-shaped area 181 of the surface. This ring-shaped area is scanned from its outer circumference 181a to its inner circumference 181b, but the measured values as such are recorded only within a given ring segment 182 which extends from the ring segment's beginning 182a to the ring segment's end 182b. The length of the ring segment, i.e. the distance from the ring segment's beginning 182a to its end 182b, and its length, i.e. the distance between the inner 181a and outer 181b circumference of the ring-shaped area 181, are always chosen in such a manner that the area 183 of the surface 10 due for measurement lies just within the ring segment.

Further, because the number of measurements obtained must be very large and the time taken to obtain them very short, the measurements are loaded at a very fast rate. This necessitates an extremely fast coordinate-transformation process. Because coordinate transformation by trigonometric computation of each positional value would take too long, a faster method is necessary. For conversion, the apparatus therefore makes use of a table 96 for coordinate transformation. For a given size of substrate, this table 96 has to be computed and stored only once. The table lists a sequence of memory addresses 97. Each address points to a space in the memory which in its turn represents a pixel 99. For each pixel 99, there may be several entries in the table, but never fewer than two.

A pointer 98 points to the current memory address 97 in the table. The current memory address contains the address of the particular pixel 99 whose location 90 (FIG. 7a) corresponds to the position of the light spot 12 on the substrate's surface 10. The value indicated by the pointer 98 is automatically incremented each time a rotation pulse 92a is received or, in detailed measurement, when an index pulse 92b is received. During measurement, the pointer thus points sequentially correctly to each memory address 97 in the table. The memory addresses are computed beforehand by coordinate transformation so as to address in its turn each pixel that corresponds to the location of the light spot 12.

The resolution of the representation of the measured result, for example of the monitor, determines the number of index pulses 92b received during the scan of a ring segment. This number can be altered by adjustment of the pulse generator's frequency 29a or of the rotary motor's speed 27.

Between two measurement-loading cycles, the light spot 12 strikes the partial area 90 on the substrate's surface. The size of this area 90 is defined by the path 901 travelled by the light spot 12 during the loading cycle in the sense of rotation 94 (X) and the feed offset 902 of the substrate during a single revolution. The size of the area 90 is less than the area of a pixel 99 projected upon the substrate's surface 10, hence during a measurement each pixel is addressed more than once to provide overlap. Near the edge of the substrate the overlap is smaller than at the substrate's centre. The analytical process takes the overlap into account as follows:

Within each pixel, all measured values that the analyzer electronics output as haze values are summed. At the same time, the apparatus stores the number of summed measurements for each pixel. When the data acquisition of measured values is complete, the sum of the measured values is divided by the number of measured values stored, in order to form a mean value. After the mean value is formed electronically, the haze values are thus averaged a second time by means of the haze filter. By contrast with the haze values, particles or LPD values are maximized. In this process, before it stores a given LPD value, the system compares it to the LPD value already present in the corresponding pixel. If the new LPD value is greater than that already stored, the apparatus deletes the old value and stores the new; if the new value is less, the apparatus discards it. Thus, in addition to the electronic formation of peak values, the LPD values are maximized a second time.

In the measurement of partial areas of the surface, the rotation pulse nearest the start of the ring segment 182a triggers the recording of measured values. The rotation pulses also make it possible to adjust the rotary motor's speed so as to generate the required number of index pulses 92 during a scan of the light spot 12 across the ring segment 182. Measured values not shown, i.e. values within the ring segment 182 but not within the area for measurement 183, are identified in the computation of the look-up table and discarded. Valid measurements obtained within the area for measurement 183 are stored and processed in the usual manner.

Figure 9:
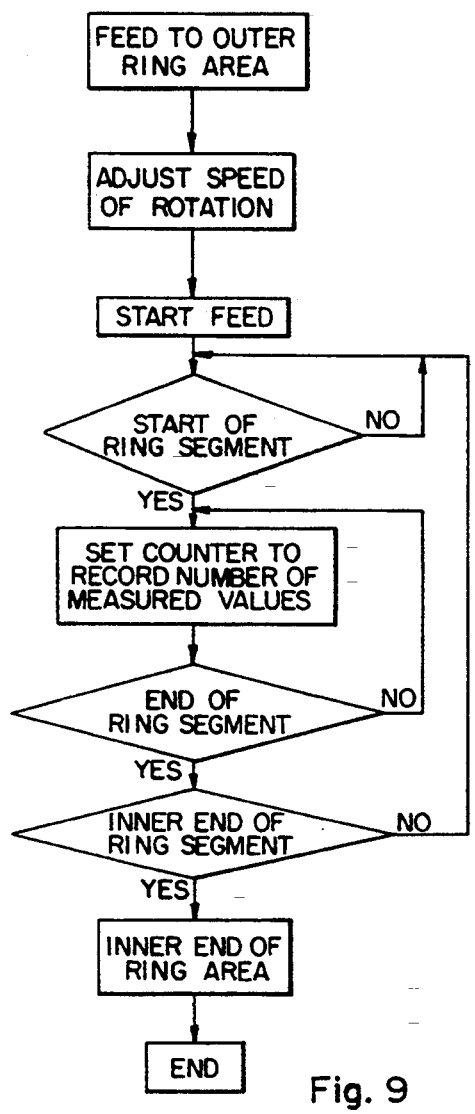
FIG. 9 is a flow chart to explain the procedure of obtaining measured values.

FIG. 9 explains this measuring process. The light spot 12 is moved to the outer circumference 181a of the ring-shaped area 181 to be measured. The speed of rotation is measured by means of the index and rotation pulses and adjusted to the required speed. When the light spot 12 arrives at the start of the ring segment 182a, each index pulse triggers the loading and storage of a measurement, as described above. A counter counts the index pulses and thus the separate measurements, and compares their number with the number previously computed from the size of the area for measurement. When the count reaches this number, the scan has arrived at the end of the ring segment. The system checks the look-up table to ensure that the scan has arrived at the end and thus at the correct radial position on the inner circumference of the ring-shaped area 181b. If not, measurement ceases until the scanning spot again arrives at the start of the ring segment 182a. Measurement and recording restart as described above. Measurement ends when the scanning spot arrives on the inner circumference of the ring-shaped area.

In measured-data acquisition, the number of revolutions during the whole of the measurement must conform to the size of the area for measurement. This number determines the feed offset between one revolution and the next, and before measurement begins it must be computed from the size of the area for measurement, the size of the light spot 12, and the resolution of the measured result. The feed offset between one revolution and the next is variable by adjustment of the translation motor's speed of rotation 28.

On conclusion of measured-data acquisition, there are two tables of measured values. One of these contains the haze values, the other the LPD values. These tables can be represented graphically, printed out, or stored.

The measured values are output as colour-coded two-dimensional graphics. Output may be either as haze graphics or LPD graphics. For colour coding 44, a given colour is assigned to a specific diffused-light amplitude range. Because the dynamic range of the measured values is greater than the number of colours available, and particularly because haze homogeneity can be extremely small in relation to the dynamic range, the excerpt of the dynamic range that is in fact represented may be chosen at will. The availability of a choice as regards the excerpt represented is also useful when analysis is to be limited to LPDs of a given size. The lower 40 and upper 41 limits of the dynamic range shown can be defined simply at the touch of a button. For user orientation, the monitor displays a movable mark 43a in a window, similar to a scroll bar.

The colour scale 44 for haze graphics 45 is chosen to represent high diffused-light amplitudes by bright red-orange colours, and low diffused-light amplitudes by dark blue-grey tints. The haze image is thus on a black background, and white areas indicate pixels whose measured value is greater than the upper limit of the dynamic range shown.

The colour scale for LPD graphics is the reverse of that for the haze graphics. The LPD image is thus on a white background. LPDs beyond the upper limit of the dynamic range shown are suppressed and appear as blank areas. For the operator's information, as in the case of the haze graphics, a movable mark in a window indicates the dynamic range shown.

Apart from colour coding, the colour scales also indicate the numerical equivalents of the measured values that each colour represents. The unit of measurement used for LPDs is the $\mu$mLSE (=micron latex-sphere equivalent), where 1 $\mu$mLSE is the diffused-light amplitude produced by a latex sphere of 1 $\mu$m diameter.

Before the system represents the $\mu$mLSE values, it computes these from a table by interpolation from standard values. The table's standard values are determined by measurement of a substrate with latex spheres of known size. The standard values need to be calibrated only once for each system.

Figure 8A:
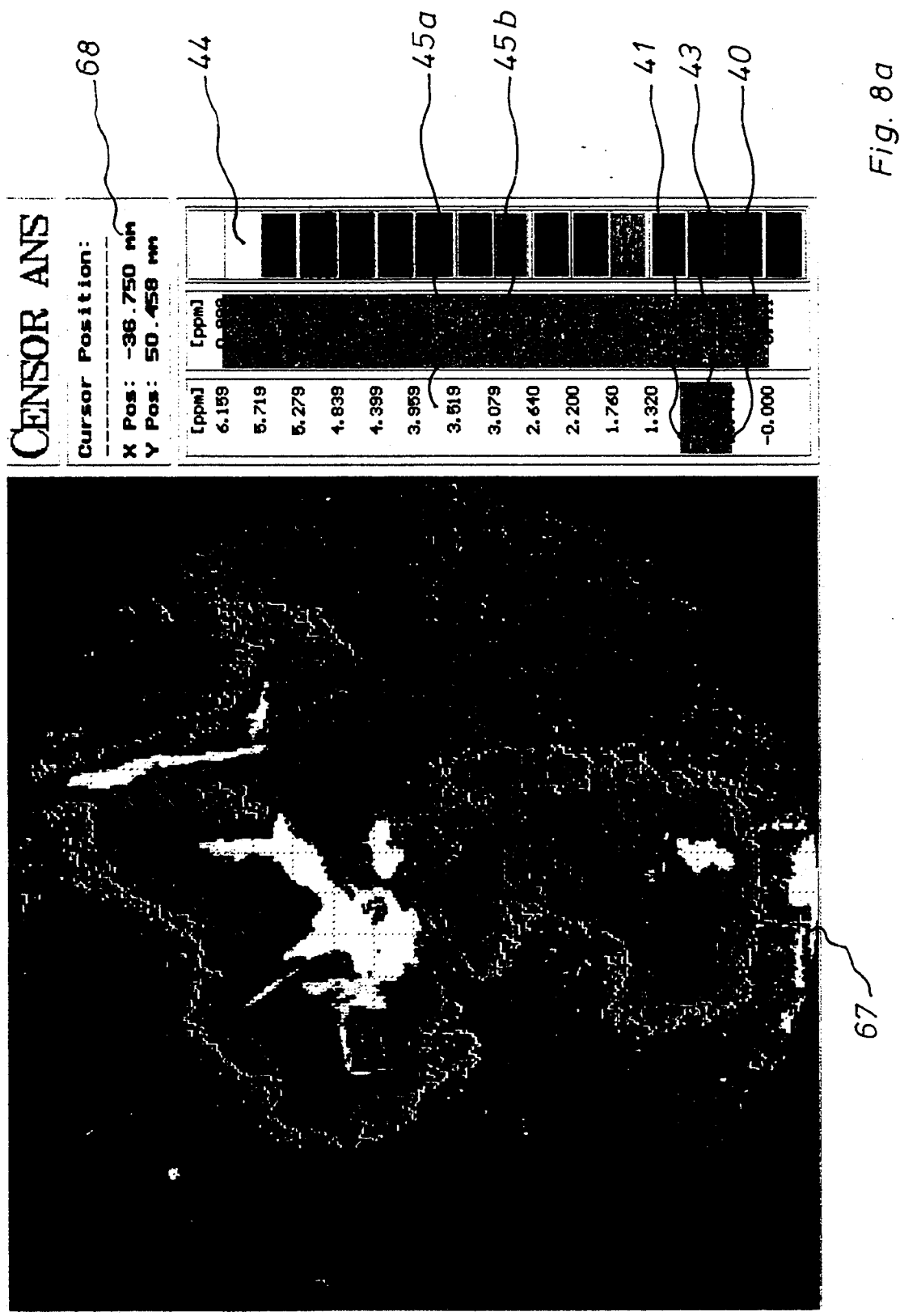
FIG. 8a is a typical measured image of the whole of a surface, with cross-hair.

The graphic display of the measurement of the whole of the surface includes a cross-hair 67 which can be moved by means of cursor-control keys (see FIG. 8a). A status panel 68 displays the coordinates of the centre of the cross-hair 67. These positional data can be used to define the site for a detailed measurement or of a defect, as may be necessary for the rapid and unequivocal location of the same site, for example in a microscope.

Figure 8B:
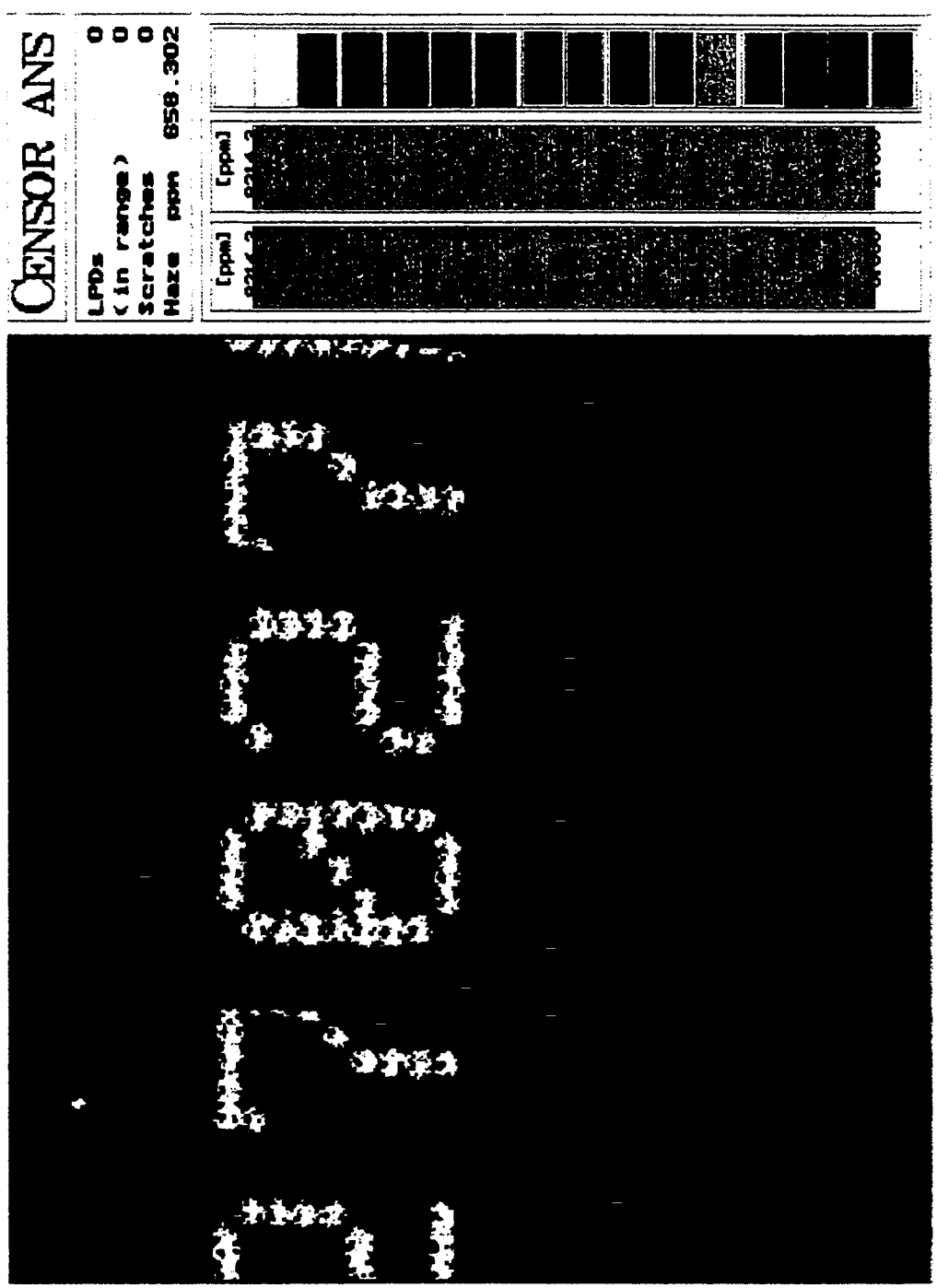

FIG. 8b shows a detailed representation of an area of the surface previously selected by means of the cross-hair 67. The figure shows laser lettering on a wafer.

Figure 8C:
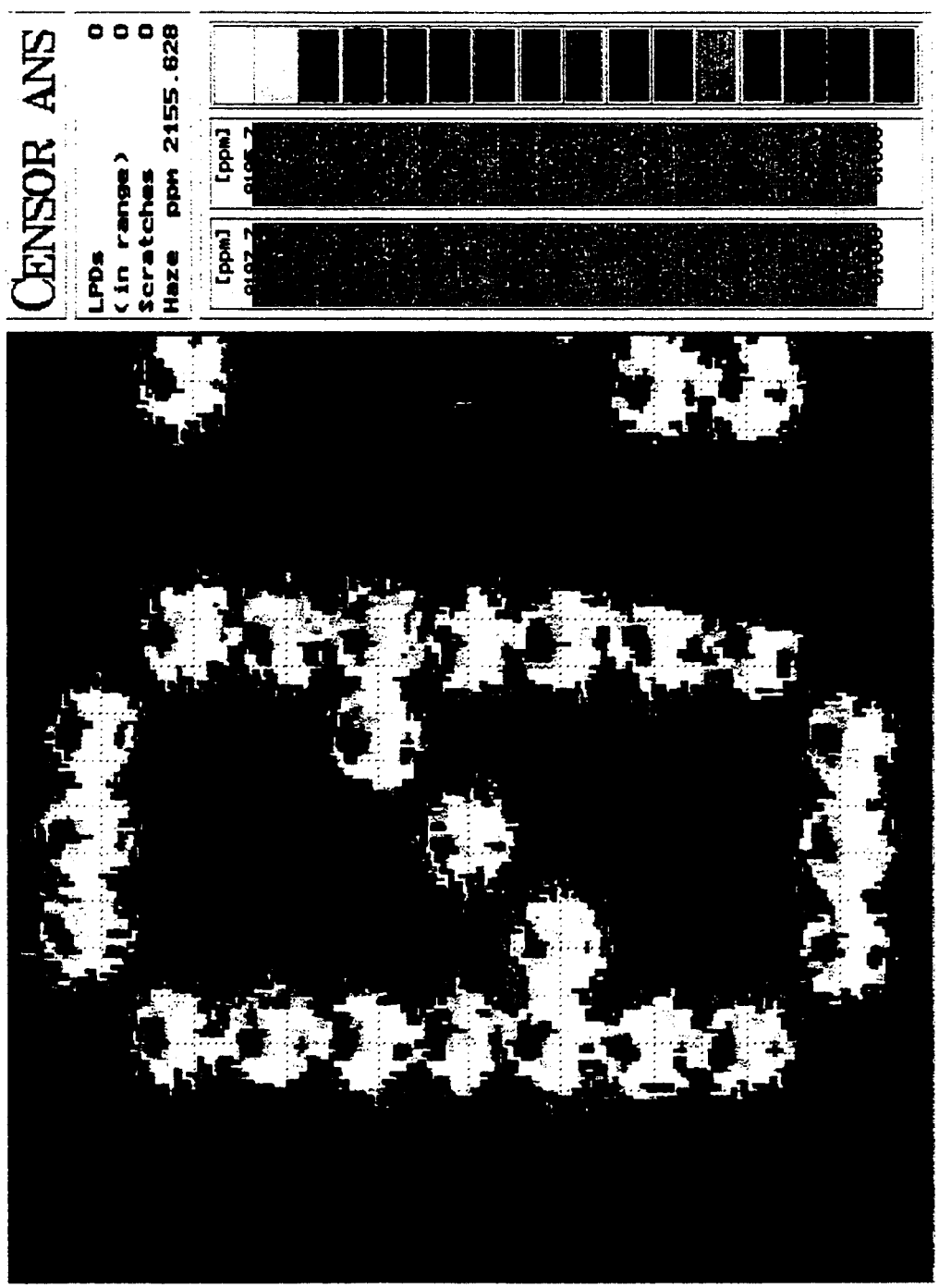
FIG. 8c is a measured image of an enlarged area of the surface of FIG. 8b.

FIG. 8c shows a further enlargement of the partial area of the surface previously selected by means of the cross-hair 67.

A histogram supplements the two-dimensional graphic representation of the surface. The histogram shows the ratio of the size or the diffused-light amplitude to the number of defects, and provides information on the statistical spread of the various type and size of defect detected.

There may be considerable differences in the surfaces of substrates measured. In practice their ability to diffuse light can vary by several orders of magnitude. This range of variation exceeds the dynamic range of the measuring system. Where the range of haze or LPDs is unforeseeable, an apparatus that automatically adjusts the measuring sensitivity by a prescale device is essential. The purpose of the prescale device is to adjust the measuring sensitivity automatically for each substrate to ensure that the measured values are always within the range of resolution provided by the apparatus.

The system described meets this requirement as follows:

Before acquisition of measured data begins, the substrate is moved far enough to ensure that the light spot no longer strikes the edge zone of the rotating substrate. While the substrate rotates, the apparatus starts with the least measuring sensitivity and gradually increases the sensitivity. It records the measured values at each step during a given period, for example during a complete revolution, and then forms a mean value. If this is less than the specified value, it automatically increases the measuring sensitivity and does another measurement cycle from which it again forms a mean. It repeats this procedure until the mean obtained corresponds to the specified value. Measurement as such begins only once the specified value has been reached.

Once the recorded and processed measured data are available, the automatic selection of the range represented is necessary. User convenience is the main consideration for this so-called autoscale function. An automatic choice of the haze range represented is made by setting the lower and upper limits 40, 41 as computed from the haze data. By computation of mean values and of erratic values from the measured values obtained, the lower and upper limits are set by displacement and scaling so as to place a certain portion of the measured values in the window 43 shown. With the right choice of window, this procedure always produces informative representations of the haze present in the substrate.

The prescale function thus simplifies the rapid examination of substrates of a wide variety of types and qualities. It ensures that all measurements are made within a logical sensitivity range, i.e. free from noise on the one hand but not saturated on the other. The autoscale function ensures that there is a clear display of the measured data. The prescale and autoscale functions combine to make the apparatus easier and more convenient to use, and increase its level of automation.

Finally, in systems of the type described, it is important to retain unchanged the well-known and established orientation of the measurements obtained. If the surface of the substrate 10 is measured without the edge zones, it is no longer possible to orient measurements in accordance with the printed-out results.

For unequivocal orientation, wafers have a flattened area or notch on the edge of the substrate. Because the system described here makes a rotary movement during measurement, an automatic orientation device can be readily implemented at little cost. This orientation device should permit the ready identification of the substrate's orientation and thus to present the results obtained by measurement at the correct orientation.

The substrate's orientation should preferably be carried out before measurement starts. When the orientation is known, all the measured results must necessarily be correctly oriented because measurement always begins at a given angle in relation to the orientation mark's position.

For orientation, the system described here uses the signal produced when the light spot 12 overruns the edge of the substrate, because the system recognizes the high amplitudes of diffused light that occur when light strikes the edge of the substrate.

Hence, for orientation, the substrate is moved until the light spot no longer strikes it. During rotation, the substrate is moved again until the light spot 12 no longer leaves its surface. This ensures that the whole of the edge zone is traced. In this procedure, the flat or notch on the substrate used for orientation produces a signal whose width diminishes in proportion to the radius. Because the dimensions of the orientation marks, the speed of rotation, and the distance travelled per revolution are all known, the signal width and its rate of decrease with each revolution permit the unambiguous identification of the orientation mark and hence the computation of its position from the above data.

To enhance the quality of the signals produced by the orientation marks, a photosensitive device 35 can be fitted under the substrate support in a fixed position relative to the substrate. During measurement of the substrate's edge zone, the photosensitive area of this device coincides approximately with the optical axis of the image-forming optics. In the measurement of the edge zone the light spot thus strikes across the orientation marks to the photosensitive area, hence the edge of the substrate and the orientation marks modulate the light of the beam 1 that strikes the photosensitive area.

In order to be capable of functioning regardless of the substrate's diameter, the photosensitive area must be oblong in shape parallel to the translation movement or must consist of several separate elements to match each substrate diameter.

The signals generated by the photosensitive device are converted into electronic signals and conducted to the electronic system described above, where they are further processed in the manner described.

Figure 10:
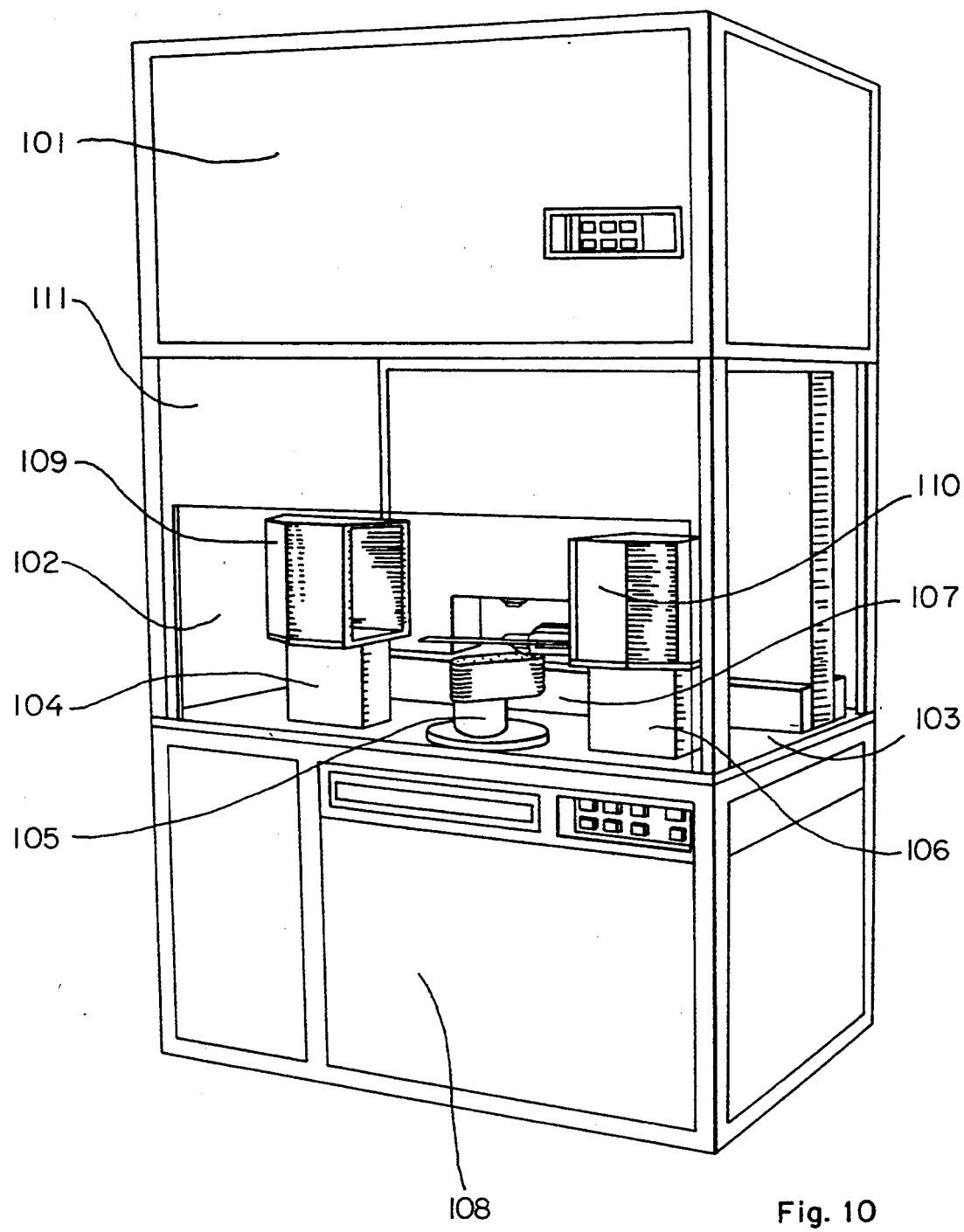
FIG. 10 is a general view of a wafer-inspection system built up on the basis of an apparatus made in accordance with the first embodiment shown in FIG. 1.

FIG. 10 shows a first wafer cassette 109 and a second wafer cassette 110. A handling robot 105 is placed between the wafer cassettes 109, 110. The apparatus described above by reference to FIG. 1 forms the main component of a measuring station 109. The wafer cassettes 109, 110, the handling robot 105, and the measuring station 107 are placed in a measuring cubicle 102. A flow box 101 above the measuring cubicle 102 supplies the whole of the measuring cubicle 102 with super-clean air to prevent any contamination of the sensitive surfaces of the wafers.

In all other respects, the measuring process is fully automatic. For this purpose, the handling robot 105 picks up a wafer from the first wafer cassette 109 and takes it to the measuring station 107 where measurement as such is performed. After measurement, the wafer is either replaced in the first wafer cassette or deposited in the second wafer cassette 110, in accordance with the result obtained.

Figure 11:
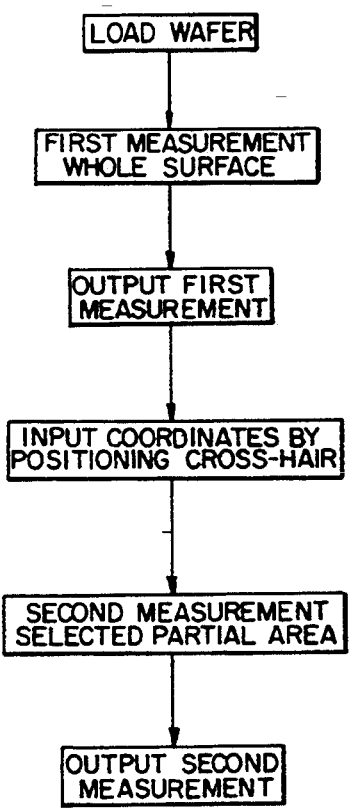
FIG. 11 is a flow chart of the measuring procedure.

FIG. 11 explains the typical measuring process. A first measurement measures and displays the whole of the surface. A movable cross-hair displayed on the monitor can be used for input of the position and size of any part of the surface that is to be examined in greater detail. In a second stage, the partial area thus selected is measured and represented.

We claim:

1. An apparatus for making high-sensitivity measurements of dot-shaped, linear, and planiform surface defects, comprising:

a light source producing a light beam;

a supporting disk on which an object having a surface to be inspected or examined is placed with the surface exposed;

an objective passing the light beam from the source perpendicularly onto the surface of the object on the supporting disk;

drive means connected to the supporting disk for moving the disk and the object thereon rotationally and translationally relative to the light beam so as to permit the light beam to scan the surface of the object along a spiral path;

a photodetector positioned to receive light reflected by the surface of the object and collected by the objective and having an output providing a signal representative of the reflected light received;

adjustable lens system means positioned on the optical path of the light beam between the light source and the objective for producing a first intermediate image of selected size and shape for a first scan of the surface of the object and a second intermediate image of selected size and shape for a second scan of the surface of the object;

said drive means also being adjustable for changing the translational movement creating the spiral path and correspondingly changing the offset of each spiral forming the path in accordance with the selected one of the intermediate images used for a scan;

a dark-field stop assembly positioned in the optical path of the light beam between the lens system means and the objective and having an adjustable dark-field deflection system whereby the light beam after deflection is centered exactly through the objective and at right angles onto the surface of the object, a confocal diaphragm placed before the photodetector to receive the light reflected by the surface of the object and collected by the objective, vignetting optics positioned along an image forming optical axis between said dark field stop assembly and said confocal diaphragm, said vignetting optics located to selectably introduce an optical asymmetry into said image forming optical axis to allow the apparatus to distinguish between the surface defects, electronic analysis means and a computer unit connected to receive output signals from the photo detector and for breaking down the output signal from the photo detector into measured values produced by dot-shaped, linear, and planiform defects in the surface of the object under inspection, and means for determining the effective scanning position of the light beam on the object surface at any time connected to the computer unit to associate the scanning positions with the measured values.

2. An apparatus in accordance with claim 31, wherein the adjustable lens system means has two lenses adjustable in relation to each other, whereof the first lens is a cylindrical lens and the second lens is a spherical lens, both lenses having the same focal length, and wherein the first intermediate image produced by the first lens is cigar-shaped with a major axis aligned with the longest dimension of said first intermediate image and a minor axis perpendicular to the major axis, and the second intermediate image produced by the second lens is dot-shaped.

3. An apparatus in accordance with claim 2, wherein the first lens is so placed in the light beam that the major axis of the cigar-shaped first intermediate image projected upon the surface of the object lies radially and the minor axis is tangential relative to the rotation of the supporting disk, so that for the first scan a greater feed offset between two successive revolutions is used than for the second scan with the dot-shaped second intermediate image.

4. An apparatus in accordance with claim 2, wherein the lenses are fitted on an L-shaped carrier plate which is pivoted between limits or end positions defined by stops on a pivot placed perpendicularly to the light beam.

5. An apparatus in accordance with claim 2, wherein the lenses are fitted to a slide and are movable in a straight line to selectively place either lens in the light beam, and adjustable stops are provided to define the position of each lens in the light beam.

6. An apparatus in accordance with claim 2, wherein the lenses are fitted to a disk which is rotatable about an axis extending parallel to the light beam, whereby the lenses are be moved alternately into the light beam by rotation of the disk by a given angular amount.

7. An apparatus in accordance with claim 1, wherein the dark-field stop assembly has a dark-field stop directly integrated in a carrier plate which is so secured to a mount as to permit adjustment of the light beam by rotation.

8. An apparatus in accordance with claim 7, wherein the dark-field stop is formed by a coating of material reflective to the light beam and placed in the centre of the dark-field stop's carrier plate along said image forming optical axis, and wherein the shape of the area of reflecting material produces a circularly symmetrical projection of the dark-field stop assembly along the optical axis, and wherein the dark-field stop's carrier plate is made of a material that transmits the light beam's wavelengths.

9. An apparatus in accordance with patent claim 8, wherein for any angle of inclination of the dark-field stop's carrier plate greater than 0°, the shape of the area of reflecting material is elliptical.

10. An apparatus in accordance with claim 1, wherein the dark-field stop assembly has a dark-field stop in the form of a prism fixed to a prism mount, the prism mount is cylindrical in shape so that the projection of the prism mount along the imaging forming optical axis is circularly symmetric, and the prism mount is fixed to a carrier plate which is adjustable and has a first opening for the entry and a second opening for the exit of the light beam.

11. An apparatus in accordance with claim 1, wherein the dark-field stop assembly has a dark-field stop in the form of a cylindrical body with an oblique surface which is silvered, and the cylindrical body is fixed to a carrier plate for the dark-field stop which is adjustable.

12. An apparatus in accordance with claim 1, wherein the vignetting optics is provided in form of a longitudinally displaceable rod to introduce asymmetry in the image.

13. An apparatus in accordance with claim 31, wherein
the means for determining the scanning position has a rotation-pulse emitter connected to a shaft of the drive means and a translation-pulse emitter connected to the computer unit, and
the rotation-pulse emitter produces angular data and the translation-pulse emitter produces radial data which permit the determination of the scanning positions by polar coordinates,
a look-up table is provided which has a number of storage positions for Cartesian coordinate addresses that correspond to the number of all pulses of the rotation-pulse emitter during a measurement, whereby addresses are stored in the storage positions to permit the determination of the XY coordinates in a Cartesian coordinate system,
a pointer is provided in the form of an address register that is automatically incremented whenever a pulse from the rotation-pulse emitter is received, so that the pointer at all times points to the currently used address in the table,
whereby the current address at any time is the address of a pixel of a Cartesian coordinate system, all of which make up a pixel area that produces the result of all measurements, and the position of each pixel in the pixel area corresponds to the position of the light spot on the surface.

14. An apparatus in accordance with claim 1, wherein the drive means has means for causing the beam to scan the surface from the center of the object towards an edge of the object.

15. An apparatus in accordance with claim 13, wherein a pulse generator is provided to generate index pulses at a selectable frequency and is connected via the computer unit to the rotation-pulse emitter, the index pulses are generated synchronously with the rotation pulses of the rotation-pulse emitter, and the number of index pulses per revolution are adjustable in accordance with the speed of rotation of the drive means.

16. An apparatus in accordance with claim 15, wherein the pulse generator is an electronic rectangular-pulse oscillator.

17. An apparatus in accordance with claim 15, wherein the electronic analysis means further including means for identifying the measured values obtained within a ring segment of the surface; and outside to be measured during the second scan for the computation of the look-up table, and means for storing the measured values that lie within the ring segment area of the surface for further processing.

18. An apparatus in accordance with claim 15, wherein the number of index pulses is greater than the number of rotation pulses, and the second scan is made at a smaller feed offset than that used for the first scan.

19. An apparatus in accordance with claim 13, wherein
display means are connected with the computer unit for displaying the measured values in a color-coded two-dimensional graph and include means for selectively displaying a haze graph and an LPD (light point defect) graph.

20. An apparatus in accordance with claim 19, wherein
the display means assigns specific colors to various diffused-light amplitudes that correspond to certain measured values.

21. An apparatus in accordance with claim 20, wherein
the display means has means for selecting a window of the dynamic range of the measurements to be displayed and represented in color, and the assignment of colors is effective within said window.

22. An apparatus in accordance with claim 19, wherein the colour scale used for the LPD graphs is the inverse colour scale for the haze graphs.

23. An apparatus in accordance with claim 19, wherein the measured values assigned to each colour also shown numerically.

24. An apparatus in accordance with claim 1, wherein display means are provided for displaying the size of the defects in the surface of the object within a selected range by means of a histogram.

25. An apparatus for surface inspections as defined in claim 1, wherein peripheral recording means is connected to the computer unit for storing the measured values obtained during measurement.

26. An apparatus for making high-sensitivity measurements of dot-shaped, linear, and planiform surface defects comprising:
a light source producing a light beam;
a supporting disk on which an object having a surface to be inspected or examined is placed with the surface exposed;
an objective passing the light beam from the source perpendicularly onto the surface of the object on the supporting disk:
drive means connected to the supporting disk for moving the disk and the object thereon rotationally and translationally relative to the light beam so as to permit the light beam to scan the surface of the object along a spiral path;
a photodetector positioned to receive light reflected by the surface of the object and collected by the objective and having an output providing a signal representative of the reflected light received;
adjustable lens system means positioned on the optical path of the light beam between the light source and the objective for producing a first intermediate image of selected size and shape for a first scan of the surface of the object and a second intermediate image of selected size and shave for a second scan of the surface of the object;
said drive means also being adjustable for changing the translational movement creating the spiral path and correspondingly changing the offset of each spiral forming the path in accordance with the selected one of the intermediate images used for a scan;
a dark-field stop assembly positioned in the optical path of the light beam between the lens system means and the objective and having an adjustable dark-field field deflection system whereby the light beam after deflection is directed exactly centered through the objective and at right angles onto the surface of the object, electronic analysis means and a computer unit connected to receive output signals from the photo detector and for breaking down the output signals from the photo detector into measured values produced by dot-shaped, linear, and planiform defects in the surface of the object under inspection, and means for determining the effective scanning position of the light beam on the object surface at any time connected to the computer unit to associate the scanning positions with the measured values, wherein the electronic analysis means has a signal input connected with an output of the photo detector and to a haze channel having a haze filter and a peak suppressor, the signal input is connected to a particle channel which has a subtraction circuit and a peak detector with a digital output, a haze-filter output is connected to the input of an analog-digital converter which has an output; and the haze filter is connected to a nominal-bandwidth input and the peak detector is connected to a second input of the electronic analysis means, whereby the measurements due to planiform defects (haze) are available at the output of the analog-digital converter, the measurements due to dot-shaped defects (LPDs) and linear defects are available at the digital output of the peak detector, and all these measurements are then loaded and stored in the computer unit.

27. An apparatus in accordance with claim 14, wherein the haze channel further comprises a low-pass filter which consists of filter condensers, resistors, and first and second switch systems, and each resistor is connected at one end via the first and second switch systems to the filter condensers and the haze-filter output, the haze-filter output is connected via a diode, which acts as a peak suppressor, to the other ends of the resistors and an output of a first amplifier, an input of a first amplifier is connected to the signal input and the non-inverting input of a second amplifier which acts as a subtraction circuit, an inverting input of the second amplifier is connected to the haze-filter output and the output of the second amplifier is connected to the input of the peak detector, for the purposes of control, the switch systems are connected to the nominal-bandwidth input, and the switch systems switch off condensers and resistors to reduce the time constant of the low-pass filter in proportion to the speed of rotation and the radial scanning position from the center of the object under inspection.

28. An apparatus in accordance with claim 26, wherein the computer unit has means for loading the measured values whenever the pulses of the rotation-pulse emitter occur and a programmable frequency-divider circuit by means whereof the number of pulses per revolution is reduced in relation to the radial distance to the center of the object surface from a surface location which receives the light beam.

* * * * *